United States Patent
Ito et al.

(10) Patent No.: US 10,457,661 B2
(45) Date of Patent: *Oct. 29, 2019

(54) METHOD OF RECOVERING LACTIDE

(71) Applicant: Toyo Seikan Co., Ltd., Tokyo (JP)

(72) Inventors: Takuro Ito, Tokyo (JP); Junko Tanabe, Yokohama (JP); Tomoaki Taguchi, Yokohama (JP)

(73) Assignee: TOYO SEIKAN CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/070,691

(22) PCT Filed: Nov. 25, 2016

(86) PCT No.: PCT/JP2016/084925
§ 371 (c)(1),
(2) Date: Jul. 17, 2018

(87) PCT Pub. No.: WO2017/130551
PCT Pub. Date: Aug. 3, 2017

(65) Prior Publication Data
US 2019/0016696 A1 Jan. 17, 2019

(30) Foreign Application Priority Data

Jan. 29, 2016 (JP) .................. 2016-015501

(51) Int. Cl.
*C07D 319/12* (2006.01)
*C08J 11/16* (2006.01)
(52) U.S. Cl.
CPC ............. *C07D 319/12* (2013.01); *C08J 11/16* (2013.01); *Y02W 30/705* (2015.05)
(58) Field of Classification Search
CPC .................................................. C07D 319/12
USPC ....................................................... 549/274
See application file for complete search history.

(56) References Cited

FOREIGN PATENT DOCUMENTS

| JP | 7-309863 | * | 11/1995 | .......... C07D 319/12 |
|---|---|---|---|---|
| JP | 7-309863 A | | 11/1995 | |
| JP | 2010-126490 A | | 6/2010 | |
| JP | 2010-126491 | * | 6/2010 | .......... C07D 319/12 |
| JP | 2010-126491 A | | 6/2010 | |
| JP | 2012-25855 | * | 2/2012 | .......... C07D 319/12 |
| JP | 2012-025855 A | | 2/2012 | |
| JP | 5051729 B2 | | 10/2012 | |
| WO | 03/091238 A1 | | 11/2003 | |
| WO | WO 2003/091238 | * | 11/2003 | .......... C07D 319/12 |

OTHER PUBLICATIONS

Sakai, Tadamoto, Plastics Age , 2012 , vol. 56 (6), 56-71.*
Tsukegi, Japanese Journal of Polymer Science and Technology, 2006, 63(4), 241-7.*
Tadamot Sakai, "Reactive Processing Technology and the Roles of the Twin-Screw Extender", Plastics Age, 2012, pp. 56-71, vol. 56, No. 6.
Takayuki Tsukegi, et al., "Recovery of Lactide from Polylactic Acid/Polyethylene Blend with Extruder", Japanese Journal of Polymer Science and Technology, 2006, pp. 241-247, vol. 63, No. 4.
Masaki Omura, et al., "Thermal Degradation Behavior of Poly(Lactic Acid) in a Blend with Polyethylene", Industrial & Engineering Chemistry Research, 2006, pp. 2949-2953, vol. 45, No. 9.
International Search Report for PCT/JP2016/084925 dated Jan. 31, 2017 [PCT/ISA/210].

* cited by examiner

*Primary Examiner* — Nizal S Chandrakumar
(74) *Attorney, Agent, or Firm* — Sughrue Mion, PLLC

(57) ABSTRACT

A method of recovering lactide which includes throwing a polylactic acid and a depolymerization catalyst into an extruder (1) communicated with a vent chamber (3) maintained under a reduced pressure, melt-kneading the polylactic acid and the depolymerization catalyst together in the extruder (1), feeding the melt-kneaded product thereof into the vent chamber (3), depolymerizing the polylactic acid in the vent chamber (3), gasifying the formed lactide and recovering the gasified lactide from the vent chamber (3).

5 Claims, 2 Drawing Sheets

METHOD OF RECOVERING LACTIDE

CROSS REFERENCE TO RELATED APPLICATIONS

This application is a National Stage of International Application No. PCT/JP2016/084925, filed on Nov. 25, 2016, which claims priority from Japanese Patent Application No. 2016-015501, filed on Jan. 29, 2016.

TECHNICAL FIELD

This invention relates to a method of recovering lactide that is formed by the depolymerization of a polylactic acid.

BACKGROUND ART

As means for solving the problem of an abnormal increase in the amount of the waste plastic materials due to an increased use of plastic materials in recent years, attention has been given to biodegradable plastic materials that undergo the decay by the action of enzymes which are released out of the bodies of bacteria and Eumycetes. Among these biodegradable plastic materials, the polylactic acid is drawing attention as an aliphatic polyester that is easily available being mass-produced on an industrial scale and that is environmentally friendly. Therefore, its use in various forms has been proposed in a wide range of fields.

The polylactic acid (PLA) is a resin made from such starting cereal starches as corns, and is a polymer obtained by the direct polycondensation of the lactide acid fermented product of starch or an L-lactic acid as a monomer, or is a polymer obtained by the ring-opening polymerization of a lactide which is a dimer of lactide. The polymer is also drawing attention as a resin of the type of a biologically completely recycling system since it can be decomposed into water and carbonic acid gas by the microorganisms present in the natural world.

As a recycling system of the polylactic acid in recent years, the greatest attention has been paid to a chemical recycling method which is capable of decomposing the polylactic acid and reusing it. This method comprises depolymerizing the polylactic acid by the heating in the presence of a depolymerization catalyst, and subjecting the obtained lactide to the ring-opening polymerization again to reuse it as the polylactic acid.

Patent documents 1 and 2 are proposing apparatuses for recovering the lactide from the polylactic acid that is applied to the chemical recycling. According to the apparatuses proposed by these patent documents, the polylactic acid, the depolymerization catalyst and the carrier resin are thrown into a biaxial extruder and are melt-kneaded therein. The melt-kneaded product is then conveyed by a screw in the biaxial extruder into a vent chamber (vent zone) where the lactide formed by the depolymerization of the polylactic acid is gasified, separated from other components and is recovered. Namely, the lactide of a low molecular weight (which is 144) formed by the depolymerization of the polylactic acid has a boiling point of as high as 255° C. under the standard atmospheric pressure. Therefore, upon feeding a melt-kneaded product that contains the polylactic acid and the depolymerization catalyst into the vent chamber maintained under a reduced pressure, the lactide that is formed can be recovered in a gasified form.

There is no problem if the lactide is recovered by using the above-mentioned recovering apparatuses on a laboratory scale. A problem, however, arouses if it is attempted to carry out the method on an industrial scale by throwing the polylactic acid in large amounts.

In the above method, for example, the depolymerization catalyst is mixed and, besides, the depolymerization is executed in an extruder accompanied, therefore, by a difficulty in controlling the temperature in the extruder and often causing the depolymerization at high temperatures. As a result, the racemization is accelerated, and the purity of the obtained lactide decreases. For example, if it is attempted to recover the L-lactide, there take place an optical isomeric transition from the L-lactide into the meso-lactide and, further, into the D-lactide due to the racemization that continues, and the purity of the desired L-lactide decreases.

In the extruder, furthermore, the carrier resin is moving while being melted and compressed, and the molten polylactic acid having a small melt viscosity and the depolymerization catalyst are conveyed by the carrier resin. Here, it has been learned by the study conducted by the present inventors that when the molten and compressed carrier resin is introduced into the vent chamber in which the pressure has been reduced, the carrier resin and the depolymerized lactide undergo the expansion since the pressure is reduced, and the carrier resin turns into a resin mass and floats on the screw conveyer passage. If the carrier resin grows into a large resin mass, the molten mixture is covered with the resin mass whereby the lactide is prevented from volatilizing. The resin mass, further, clogs the flow passage of the gaseous lactide formed by the depolymerization of the polylactic acid, and causes a great decrease in the efficiency for recovering the lactide. Moreover, the resin mass scatters and mixes into the lactide that is trapped from the vent chamber causing, therefore, serious problems.

The state where the lactide is allowed to volatilize little or is prevented from volatilizing due to the mass of the carrier resin is, usually, called "vent-up".

PRIOR ART DOCUMENTS

Patent Documents

Patent document 1: JP-A-2010-126490
Patent document 2: Japanese Patent No. 5051729

OUTLINE OF THE INVENTION

Problems That the Invention is to Solve

It is, therefore, an object of the present invention to provide a method of recovering lactide, which is capable of recovering, in a highly pure form, the lactide formed by the depolymerization of a polylactic acid.

Another object of the invention is to provide a method of recovering lactide, which is capable of efficiently recovering the lactide effectively avoiding the formation of resin masses and without permitting the occurrence of the vent-up.

Means for Solving the Problems

According to the present invention, there is provided a method of recovering lactide comprising throwing a polylactic acid and a depolymerization catalyst into an extruder, melt-kneading the polylactic acid and the depolymerization catalyst together in the extruder, feeding the melt-kneaded product thereof from the extruder into a vent chamber maintained under a reduced pressure, depolymerizing the polylactic acid in the vent chamber, gasifying the formed lactide therein, and recovering the gasified lactide from the vent chamber.

In the method of recovering lactide of the present invention, it is desired that:

(1) The polylactic acid and the polymerization catalyst are thrown into the extruder but without throwing the carrier resin therein, and the melt-kneaded product of the polylactic acid is fed into the vent chamber without using the carrier resin;

(2) A trapping apparatus is linked to the vent chamber to trap the gasified lactide;

(3) The vent chamber is provided at the bottom portion thereof with a discharge pipe for discharging the residue from which the gasified lactide has been removed;

(4) The depolymerization catalyst is thrown into the extruder on the side downstream of the polylactic acid in the direction of extrusion in the extruder; and (5) The temperature in the extruder is so set that the temperature of a melt of the polylactic acid is not higher than 270° C. at the discharge port of the extruder, and the interior of the vent chamber is so set that the pressure is not higher than 8 kPaA and the temperature is 250 to 330° C.

Effects of the Invention

In the present invention, the polylactic acid and the depolymerization catalyst are melt-kneaded in the extruder, and the polylactic acid is depolymerized in the vent chamber where the formed lactide is gasified, the vent chamber being communicated with the extruder.

When the polylactic acid is depolymerized in the extruder, the lactide that is formed by the depolymerization tends to be racemized; i.e., it is difficult to obtain the lactide in a highly pure form free of optical isomers thereof. In the extruder, the melt-kneaded product containing the polylactic acid is conveyed by the extrusion screws and, therefore, a gap is narrow between the screws and the cylinder wall. When the heating is executed by using a heater mounted in the cylinder wall, it becomes very difficult to adjust the melt-kneaded product in the extruder. This is because the melt-kneaded product is heated by the external heating due to the heater (cylinder wall) and by the internal heating (heat due to the shearing) generated by the turn of the extrusion screws. Therefore, the polylactic acid is, in many cases, locally heated to unnecessarily high temperatures, and the depolymerization at high temperatures causes the lactide that is formed to be racemized.

According to the present invention, on the other hand, the polylactic acid is not depolymerized in the extruder but is depolymerized in the vent chamber in which the temperature can be easily controlled unlike that in the extruder. Therefore, the lactide that is formed is effectively prevented from being racemized and can be recovered in an optically highly pure form.

Further, the present invention offers a great advantage of recovering the lactide using no carrier resin. The polylactic acid can be extruded at a low resin temperature, i.e., having a relatively high melt viscosity as compared to when the depolymerization is conducted in the extruder. Therefore, the molten resin can be conveyed without using the carrier resin and, besides, the sealing between the extrusion screws and the cylinder wall can be maintained by the molten resin.

Namely, the present invention executes the step of recovering the lactide without using the carrier resin which could turn into resin masses that might trigger the vent-up. This means that the present invention reliably prevents such problems as clogging in the vent chamber and mixing of resin masses into the lactide that is trapped. These are great advantages of the present invention.

MODES FOR CARRYING OUT THE INVENTION

Figure 1:
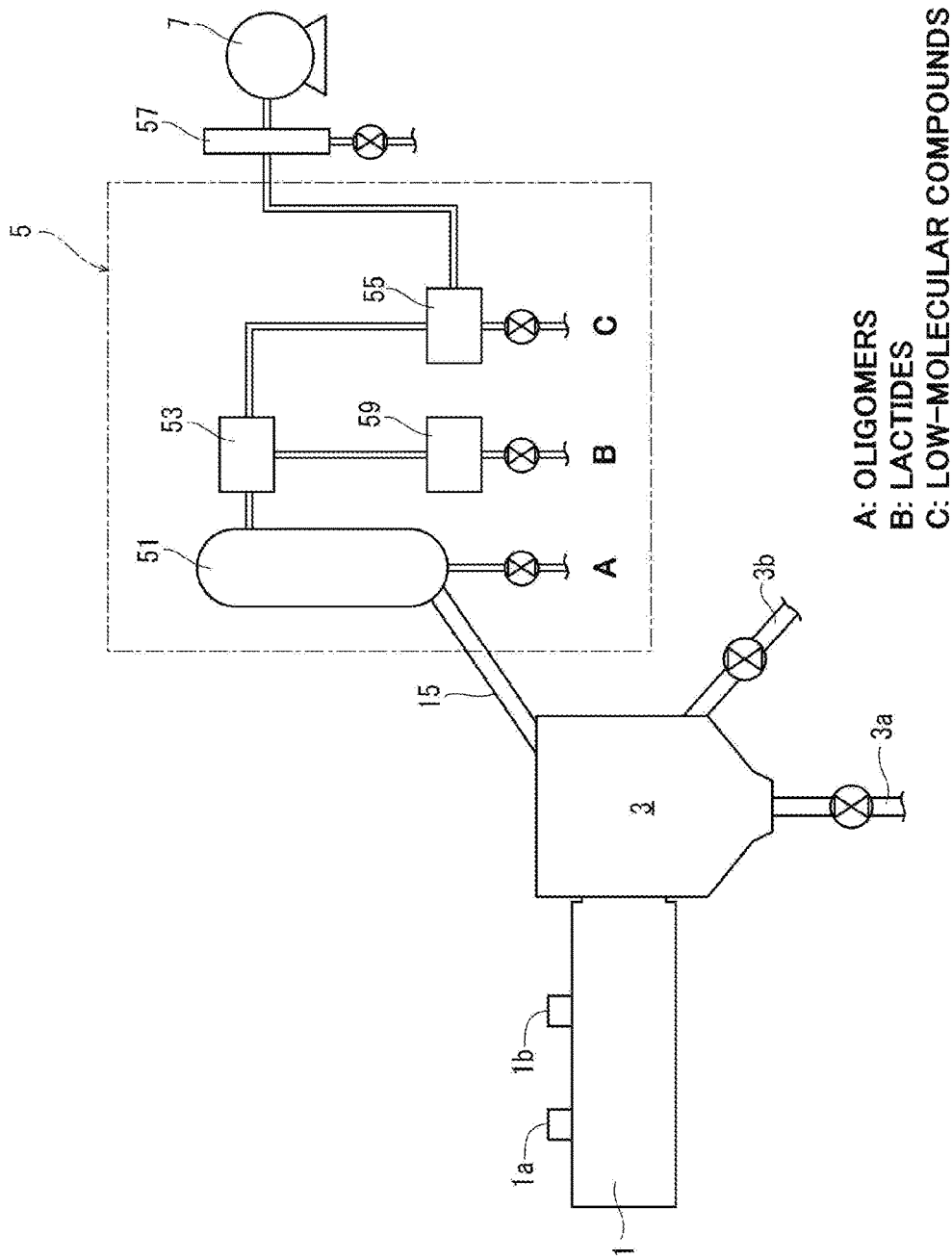
[FIG. 1] It is a drawing schematically illustrating the structure of a recovering apparatus used for favorably carrying out a recovering method of the present invention.

Referring to FIG. 1, roughly speaking, a recovering apparatus used for carrying out the method of recovering lactide of the present invention comprises an extruder (melt-kneading apparatus) 1, a vent chamber 3 communicated with the extruder 1, and a trapping apparatus 5 communicated with the vent chamber 3. Usually, the interior of the vent chamber 3 is maintained under a predetermined reduced pressure due to a vacuum pump 7 provided on the side of the trapping apparatus 5.

The present invention uses the above-mentioned recovering apparatus. Namely, a polylactic acid, a depolymerization catalyst and, as required, a carrier resin are thrown into the extruder 1, and are melt-kneaded in a cylinder of the extruder 1. The melt-kneaded product (molten resin) thereof is then fed into the vent chamber 3 where the polylactic acid is depolymerized, and a lactide formed by the depolymerization of the polylactic acid is gasified. The gasified lactide is then introduced into the trapping apparatus 5 from the vent chamber 3 through a trapping tube 15, is liquefied through a gas-liquid separation tower 51 and a first condenser 53, and is recovered through a receiver 59.

As the polylactic acid from which the lactide is to be recovered, there can be used those recovered from the market (post-consumer wastes), industrial wastes discharged from the resin processing manufacturers and out-of-specification resins generated in the step of producing polylactic acid resins. There can be, further, used those of the stereocomplex type in which L-lactic acid (PLLA) and D-lactic acid (PDLA) are mixed together, or those of the meso type in which L-lactic acid unit and D-lactic acid unit are present in a mixed manner in the molecular chains. Use of a virgin polylactic acid poses no problem, as a matter of course.

Moreover, the polylactic acid that is used may include small amounts of copolymer units, e.g., may include units due to lactones, cyclic ethers, cyclic amides, alcohols or carboxylic acids, that are capable of copolymerizing with the lactide under the condition that not less than 50 mol % thereof are the lactic acid units.

MgO is a representative example of the catalyst for depolymerizing the polylactic acid, and is most preferably used. However, there can also be used such alkaline earth metal oxides as CaO, SrO, BaO and the like. There can be, further, preferably used Sn(II) 2-ethylhexanoate which is used as the polymerization catalyst and aluminum hydroxide $(Al(OH)_3)$ which is a flame retarder. It is also allowable to use these catalysts as a mixture thereof. The depolymerization catalyst works to lower the temperature for depolymerizing the polylactic acid. Upon using the depolymerization catalyst, thermal decomposition of the polylactic acid is accelerated, and the polylactic acid starts acquiring decreasing molecular weights. For instance, the polylactic acid that possessed a molecular weight of about 200,000 when it was thrown into the hopper of the extruder 1 can be decomposed into a lactide of a molecular weight of 144. Further, MgO and the like are effective in suppressing the racemization phenomenon during the thermal reaction, and are most favorably used in the present invention.

The catalyst for depolymerizing the polylactic acid is used, usually, in an amount of 0.1 to 5 parts by mass per 100 parts by mass of the polylactic acid.

As the carrier resin that is used as required, there can be used various thermoplastic resins so far as they do not adversely affect the depolymerization of the polylactic acid and do not show reactivity to the lactide that is formed by the depolymerization of the polylactic acid. Usually, however, there can be favorably used olefin resins such as high-density polyethylene (HDPE), low-density polyethylene (LDPE), polypropylene (PP) and the like; polyester resins such as polyethylene terephthalate (PET) and the like; polyethers such as polycarbonate (PC) and the like; and styrol resins such as polystyrene (PS) and the like. Among them, there can be favorably used HDPE, LDPE and PP having high melt viscosities.

Figure 2:
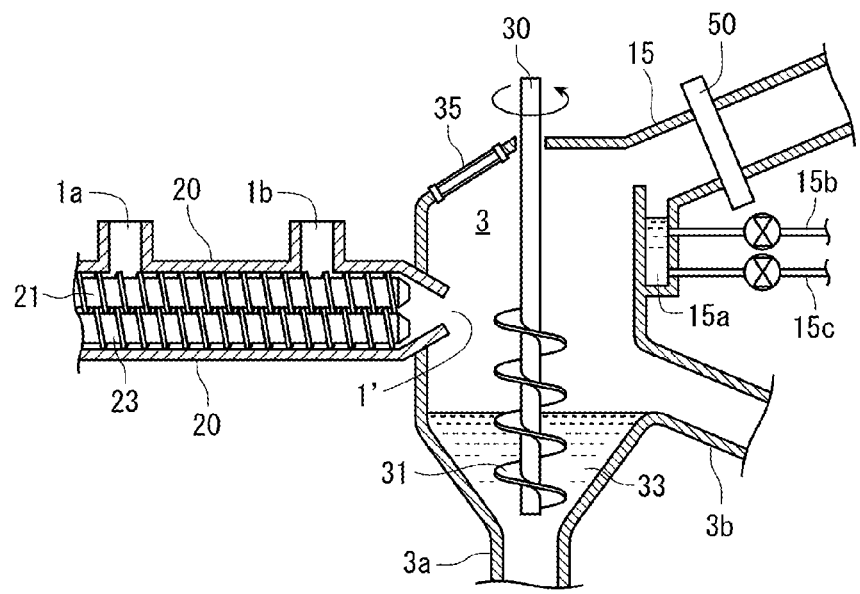
[FIG. 2] It is a view illustrating in cross section the structure of an extruder and a vent chamber in the recovering apparatus of FIG. 1.

Reference is now made to FIG. 2 which illustrates in cross section the structure of the extruder 1 and the vent chamber 3. The above-mentioned polylactic acid, depolymerization catalyst and carrier resin that is used as required are thrown into the extruder 1 which is communicated at its end with the vent chamber 3.

In FIG. 2, the extruder 1 has a biaxial structure with extrusion screws 21 and 23 provided in a cylinder wall 20. It is also allowable, as a matter of course, to use a monoaxial extruder having a short-axis structure with only one extrusion screw.

The extruder 1 has two hoppers 1a and 1b, the hopper 1a being positioned on the upstream side and the hopper 1b on the downstream side with respect to the direction of extrusion by the extrusion screws 21 and 23.

A discharge port 1' at an end of the extruder 1 has a shape that is tapered to become narrow toward the end thereof, though the shape is not limited thereto only. The discharge port 1' is extending into the vent chamber 3. Therefore, the molten resin is allowed to be smoothly extruded into the vent chamber 3 while effectively maintaining the sealing so that the degree of vacuum is not impaired in the vent chamber 3.

Further, though not shown, the cylinder wall 20 is fitted with a heater which heats the interior of the extruder 1. In the present invention, the interior of the extruder 1 is heated to such a temperature that is higher than the temperature at which the polylactic acid that is thrown into the extruder 1 melts but that does not cause the depolymerization. Namely, the interior of the extruder 1 is so heated that the temperature of the resin at, for example, the discharge port 1' of the extruder 1 is not higher than 270° C., specifically, is in a range of 170 to 270° C. and, more preferably, 200 to 255° C.

If the temperature of the molten resin extruded from the discharge port 1' of the extruder 1 is unnecessarily high, then the polylactic acid undergoes the thermal decomposition in the extruder 1 or the lactide that is formed tends to be racemized. Moreover, if the molten resin of a high temperature is fed into the vent chamber 3, the temperature in the vent chamber 3 becomes out of control, and the lactide that is formed often tends to be more easily racemized. Moreover, if the temperature of the molten resin is too low at the discharge port 1', the resin that has not been melted may often be contained, and the polylactic acid and the depolymerization catalyst may not often be kneaded together to a sufficient degree. It is, therefore, desired that the interior of the extruder 1 is so heated that the temperature of the resin lies within the above-mentioned range at the discharge port 1' of the extruder 1.

Here, despite the temperature of the resin at the discharge port 1' is set to be not higher than 270° C. as described above, if viewed on a microscopic scale, very small amounts of the polylactic acid may often be heated to a temperature in excess of 270° C. on the surfaces contacting to the extrusion screws 21 and 23 due to the heat of shearing generated by the turn of the screws. In the present invention, however, even if the polylactic acid heated to such a high temperature comes in contact with the depolymerization catalyst, its residence time in the extruder 1 is very short; i.e., the polylactic acid is readily released into the vent chamber 3. Therefore, even if the polylactic acid is heated to such a high temperature in trace amounts, the degree of racemization is on a negligible level.

The above-mentioned polylactic acid, depolymerization catalyst and carrier resin that is used as required are thrown into the extruder 1 of which the interior has been so heated that the temperature of the resin at the discharge port 1' lies in the above-mentioned range, and are melt-kneaded together therein, conveyed by the extrusion screws 21 and 23, and are, further, extruded from the discharge port 1' into the vent chamber 3 in which the pressure has been reduced.

It is here desired that the polylactic acid and the carrier resin that is used as required are thrown in through the hopper 1a on the upstream side while the depolymerization catalyst is thrown in through the hopper 1b located on the downstream side.

That is, if the polylactic acid and the depolymerization catalyst are heated at a high temperature in a state of being contacted to each other, then the lactide formed through the depolymerization may undergo the racemization and the purity of the lactide that is recovered may decrease. The temperature in the extruder 1 has been so set that the depolymerization will not take place. In principle, therefore, there takes place neither the depolymerization nor the racemization. As will be learned from FIG. 2, however, the extrusion screws 21 and 23 have been provided in the extruder 1, and the polylactic acid and the like are thrown into a very narrow space between the cylinder wall 20 and the extrusion screws 21, 23 where they are melt-kneaded together, and the kneaded product is melt-extruded. Therefore, it is very difficult to adjust the temperature of the kneaded product. Specifically, heat of shearing generates due to the turn of the extrusion screws 21, 23, and the kneaded product might often be locally heated to a considerably high temperature. If the depolymerization catalyst is present in the melt that is heated to such a high temperature, the depolymerization takes place locally and, besides, the lactide that is formed by the depolymerization undergoes the racemization.

By throwing the depolymerization catalyst into the hopper 1b on the downstream side, however, the residence time of the depolymerization catalyst can be shortened and the time in which the melt is placed in a high-temperature state in the presence of the depolymerization catalyst can be greatly shortened irrespective of if the locally highly heated state has occurred. Therefore, despite the lactide is formed by the depolymerization, the lactide can be more effectively prevented from being racemized.

To reliably prevent the racemization, a method can be contrived to feed the depolymerization catalyst into the vent chamber 3. This method, however, is not employable. This is because the mixing/stirring capability in the vent chamber 3 is very poorer than that in the extruder 1. Therefore, it is difficult to bring the polylactic acid and the depolymerization catalyst into even and homogeneous contact with each other, and the depolymerization cannot be effectively carried out.

The present invention, further, requires the use, in decreased amounts, of the carrier resin that is indispensable in the ordinary recovering methods or does not at all requires the use of the carrier resin, i.e., the recovering method without using any carrier resin.

That is, the polylactic acid containing the lactide, usually, has a melt viscosity which is considerably lower than those of ordinary polymers though dependent upon the molecular weight thereof. Usually, therefore, the melt of the polylactic acid cannot be efficiently conveyed by the screws. This is because the screws turn nearly idle. In an ordinary recovering method, therefore, a carrier resin is used in combination to increase the viscosity of the molten resin that contains the melt of the polylactic acid in the extruder and, therefore, to efficiently convey the melt of the polylactic acid by the screws. Further, the carrier resin has a melt viscosity higher than that of the polylactic acid that contains the lactide. By melting and mixing the carrier resin in not less than a certain amount with the polylactic acid, therefore, it is made possible to convey the molten mixture by screws maintaining a state where the gap between the inner surface of the cylinder 20 of the extruder 1 and the screws 21, 23 is filled with the molten mixture. That is, use of the carrier resin makes it possible to maintain a state where the gap is always sealed between the inner surface of the cylinder 20 and the screws 21, 23 and, therefore, the pressure in the vent chamber 3 can be effectively reduced.

By using the carrier resin as described above, the melt of the polylactic acid can be effectively conveyed (extruded) and, besides, the pressure in the vent chamber 3 can be maintained reduced. A generally employed method uses the carrier resin in an amount of not less than 150 parts by mass per 100 parts by mass of the polylactic acid. According to the present invention, however, no depolymerization is carried out in the extruder 1 and, accordingly, the resin temperature is set to be not higher than 270° C. at the discharge port 1' of the extruder 1. It is, therefore, made possible to recover the lactide by using the carrier resin in a decreased amount or without using the carrier resin.

That is, since the temperature has been set to be low in the extruder 1, the polylactic acid that is melted in the extruder 1 has a high melt viscosity. As a result, the amount of the carrier resin can be decreased to be, for example, less than 20 parts by mass. Moreover, even without using the carrier resin, the polylactic acid can be effectively conveyed by screws yet maintaining the sealing and reduced pressure in the vent chamber 3.

In the present invention, further, when the carrier resin is used in a decreased amount or is not quite used, the running cost can be decreased, which is very advantageous. Besides, formation of resin masses that could cause the vent-up can be prevented, which is also very advantageous for carrying out the method of the invention on an industrial scale.

The molten resin containing the polylactic acid and the depolymerization catalyst is extruded into the vent chamber 3 in which the pressure is maintained reduced, the polylactic acid is depolymerized, and the lactide formed by the depolymerization thereof is gasified.

The vent chamber 3 has the shape of a funnel as a whole so that the polylactic acid is depolymerized and the lactide formed by the depolymerization thereof is effectively gasified. The heater (not shown) fitted in the outer wall of the vent chamber 3 heats and maintains the molten resin (designated at 33 in FIG. 2) at a temperature of 250 to 330° C. and, specifically, 270 to 320° C. Moreover, the vacuum pump 7 works to reduce the pressure down to be not higher than 8 kPaA and, specifically, 0.1 to 8 kPaA. If the resin temperature in the vent chamber 3 becomes lower than the above range, then the lactide may not be formed. If the resin temperature exceeds the above range, on the other hand, the lactide may be racemized much and the lactide that is recovered may have a decreased optical purity.

The vent chamber 3 is provided with a stirring shaft 30 that extends up and down in the central portion thereof. The stirring shaft 30 has a spiral stirring blade 31 that works to stir the molten resin 33 fed from the extruder 1, whereby the polylactic acid is depolymerized and the lactide that is formed is effectively gasified.

That is, in the vent chamber 3, the molecular weight of the polylactic acid continues to decrease due to the depolymerization, and there is obtained a lactide (dimer of lactic acid) that constitutes the basic unit of the polylactic acid. Here, the lactide has a boiling point which is 255° C. under the standard atmospheric pressure where, however, the lactide lies in a boundary region of liquid-gas phase separation where it is difficult to trap the gas maintaining stability. Namely, in the state where the lactide remains liquid, it is not allowed to separate the lactide from the molten carrier resin efficiently and stably. As described above, therefore, the interior of the vent chamber 3 is maintained under a reduced pressure so that the lactide acquires a decreased boiling point and is gasified in an accelerated manner.

It is, further, desired that two discharge pipes 3a and 3b are linked to the bottom portion of the vent chamber 3.

One discharge pipe 3a is linked to the bottom portion of the vent chamber 3. The residue of the molten resin 33 (residual catalyst, the carrier resin used as required, etc.) from which the lactide has been removed by being gasified is discharged through the discharge pipe 3a provided in the bottom portion of the vent chamber 3, and is discarded. The vent chamber 3, desirably, has the shape of a funnel as a whole as shown in FIG. 2 from the standpoint of improving the efficiency for stirring the molten resin 33 and also from the standpoint of effectively discharging the residue through the discharge pipe 3a.

The other discharge pipe 3b is linked to the side wall of the vent chamber 3 to remove impurities of small specific gravities that are present on the surface portions of the molten resin 33. The polylactic acid used in the method of the present invention is, usually, blended with various additives which include those having specific gravities smaller than that of the polylactic acid. Among the carrier resins that are used as required, further, the polyethylene terephthalate (PET) and the like have specific gravities larger than that of the polylactic acid whereas the olefin resin and the like have specific gravities smaller than that of the polylactic acid. The impurities having such small specific gravities may float on the surface of the molten resin 33 in the vent chamber 3. The lactide that is formed is gasified while stirring the molten resin 33, and presence of the impurities having such small specific gravities is not much of a problem. The impurities having small specific gravities that float in increased amounts on the surface, however, may hinder the lactide from gasifying. Therefore, the discharge pipe 3b is provided on the upper side of the side wall of the vent chamber 3 to suitably remove the impurities of small specific gravities floating on the surface of the molten resin 33.

When the depolymerization is carried out by using the carrier resin and the lactide is gasified in a manner that has heretofore and generally been employed, the carrier resin turns into a massive form which prevents the lactide from gasifying or enters into the trapping tube 15 to develop vent-up. In the present invention as described earlier, however, the carrier resin is used in a decreased amount or is not used making it, therefore, possible to effectively or reliably avoid such a problem.

The lactide that is gasified in the vent chamber 3 is introduced into the trapping apparatus 5 through the trapping tube 15 provided at the upper wall (or ceiling wall) of the vent chamber 3. Here, as shown in FIG. 2, the trapping tube 15 is extending being tilted upward and is provided with a vacuum break prevention valve 50 which is opened or closed in case of abnormal condition.

It is, further, desired to provide a receiving vessel 15a near the inlet portion of the trapping tube 15 to receive the refluxing liquid. Namely, the lactide liquefied in the trapping tube 15 is trapped in the receiving vessel 15a and does not flow down into the vent chamber 3. This is desirable in preventing the lactide from being racemized. This is because the lactide may undergo the racemization after it is liquefied and gasified repetitively.

The receiving vessel 15a is provided with a vacuum break/restore line 15b and a recovering line 15c for maintaining the pressure reduced in the vent chamber 3 and for recovering the lactide that has refluxed into the receiving vessel 15a.

The ceiling wall of the vent chamber 3, as shown in FIG. 2, is desirably tilting down toward the outer side in the radial direction. It is desired that the above tilted wall is provided with a peep window 35 for observing the interior of the vent chamber 3. That is, the gasified lactide may be cooled into a liquid thereof by the ceiling portion or by the peep window 35 in the vent chamber 3, and may form a refluxing liquid thereof. The above structure is to prevent the refluxing liquid from mixing into the molten resin 33 so that the lactide will not be liquefied and gasified repetitively. It is, therefore, desired that the peep window 35 is a double window having improved heat retaining property to prevent the lactide from liquefying. Though not shown in FIG. 2, it is also desired to provide a receiving vessel on the side wall of the vent chamber 3 to recover the refluxing liquid like in the case of the above-mentioned trapping tube 15.

In the trapping apparatus 5 to which the above-mentioned trapping tube 15 is linked, there are provided a gas-liquid separation column 51, a first condenser 53, a second condenser 55 and a chilling trap 57. Impurities are removed by gas-liquid separation from the gaseous product of lactide collected from the vent chamber 3, and the lactide is recovered in a highly pure form. That is, the gaseous product of lactide collected from the vent chamber 3 contains various low molecular compounds derived from the oligomers of the lactic acid and from the lubricating agent contained in the polylactic acid or the carrier resin, in addition to containing the lactide. Therefore, these impurities must be removed.

Concretely, the lactide recovered in a gaseous form is passed through the gas-liquid separation column (rectification column) 51 to remove high molecular oligomer components through the demister in the gas-liquid separation column. Thereafter, the lactide is introduced into the first condenser (heat exchanger) 53 where the lactide only is subjected to the phase conversion (phase change) so as to be recovered as liquid lactide.

A proper heat-exchange temperature in the phase conversion varies depending on the degree of vacuum. Usually, under the standard atmospheric pressure, the lactide (L-lactide/D-lactide) has a boiling point and a melting point which are, respectively, 255° C. and 92° C. to 94° C. Therefore, the heat-exchange temperature is, preferably, 60° C. to 140° C. in a vacuum range of 0.1 KPaA to 8 KPaA. More preferably, the heat-exchange temperature is 80° C. to 100° C. in a vacuum range of 0.5 KPaA to 4 KPaA.

If lower than 0.1 KPaA, for example, the degree of vacuum is so high that the lactide gas passes at a too high speed through the gas-liquid separation column 51 and the first condenser 53. Therefore, a sufficient period of time is not provided for the exchange of heat, and the lactide may possess a decreased purity and may be recovered in a decreased efficiency. If higher than 8 KPaA, on the other hand, the degree of vacuum is so low that the boiling point of the lactide is not lowered to a sufficient degree, the lactide is not gasified to a sufficient degree, and the recovering efficiency tends to decrease.

If the heat-exchange temperature is lower than the above range, further, the low-boiling impurities tend to be liquefied, and the purity of the recovered lactide may decrease. If the heat-exchange temperature is higher than the above range, on the other hand, the lactide is not easily liquefied and, therefore, tends to be recovered in a decreased efficiency.

Further, in order to recover the depolymerized product (lactide) of the polylactic acid in the gaseous form, it is desired that the facilities (gas-liquid separation column 51, first condenser 53, second condenser 55, etc.) in the trapping apparatus 5 are installed at positions higher than the vent chamber 3.

The gas from which the oligomers are removed is cooled through the first condenser (heat exchanger) 53 down to about 90° C. whereby the desired lactide is liquefied and is recovered in the receiver 59. The remaining gas is cooled through the second condenser (heat exchanger) 55 down to about 5° C. whereby low-boiling low-molecular compounds are removed. Finally, the gas is cooled through the chilling trap 57 down to about −50° C., and the residual compounds, too, are removed in the form of a liquid.

The liquid collected in the bottom of the above-mentioned receiving vessel 15a can be directly discarded. Or, if there is no problem, the liquid can be introduced into the step of refining together with the liquid lactide recovered in the receiver 59.

Figure 3:
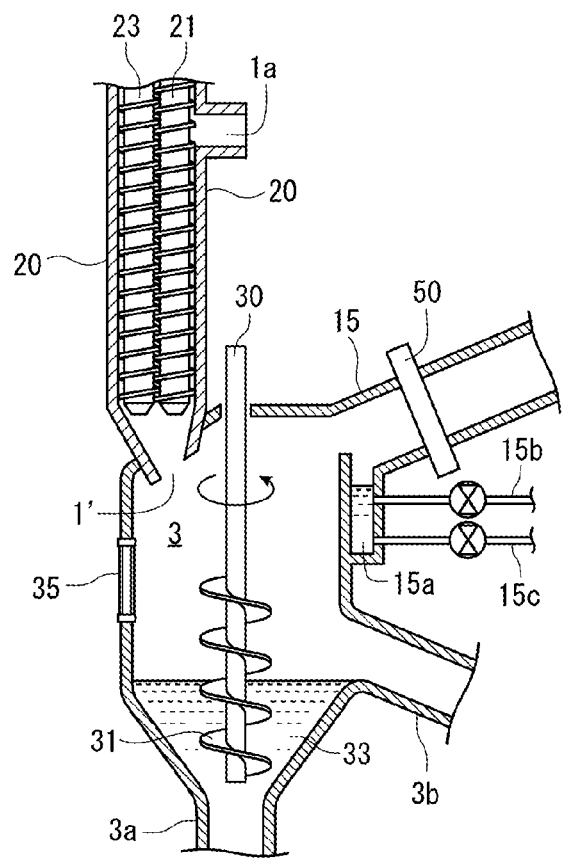
[FIG. 3] it is a view schematically illustrating in cross section another structure of the extruder and the vent chamber in the recovering apparatus of FIG. 1.

In the above-mentioned embodiment shown in FIGS. 1 and 2, the extruder 1 is extending in a horizontal direction. The extruder 1, however, may extend tilted and linked to the vent chamber 3, or may extend up and down (in the vertical direction) and linked to the vent chamber 3. FIG. 3 shows an embodiment in which the extruder 1 is extending up and down.

Namely, the molten resin 33 is extruded like a rope from the discharge port 1' of the extruder 1. When the extruder 1 is provided being tilted or is extending in the vertical direction as shown in FIG. 3, there is obtained an advantage in that the molten resin 33 extruded like the rope does not drip down along the side wall of the vent chamber 3 but is fed smoothly into the vent chamber 3.

In FIG. 3, the basic structure is the same as that of the apparatus shown in FIG. 2, and the members are all denoted by the same numerals. In the embodiment of FIG. 3, for example, the peep window 35 is provided in the side wall that is extending in the vertical direction. In this case, too, like in the trapping tube 15, it is desired that the receiving vessel is provided in the side wall under the peep window 35 to recover the refluxing liquid of lactide that is formed as it is cooled by the peep window 35.

In the recovering method of the present invention that is carried out by using the above-mentioned apparatus, it is desired that the molten resin is depolymerized and the lactide is gasified in the vent chamber 3 continuously while feeding the molten resin containing the polylactic acid from the extruder 1 into the vent chamber 3. It is, however, also allowable to recover the lactide batchwise. That is, the molten resin is fed in a predetermined amount into the vent chamber 3, and the extruder 1 is halted. In this state, the molten resin is depolymerized and the lactide is gasified in the vent chamber 3.

According to the present invention described above, it is made possible to effectively prevent the lactide from being racemized and to recover the lactide in a highly pure form. It is, further, made possible to reduce the amount of the carrier resin that is used or not to use the carrier resin.

DESCRIPTION OF REFERENCE NUMERALS

1: extruder
1': discharge port of the extruder
3: vent chamber
3a, 3b: discharge pipes
5: trapping apparatus
7: vacuum pump
15: trapping tube
15a: receiving vessel
20: cylinder wall
21, 23: extrusion screws
30: stirring shaft
33: molten resin
35: peep window
51: gas-liquid separation column
53: first condenser
55: second condenser

The invention claimed is:

1. A method of recovering lactide comprising throwing a polylactic acid and a depolymerization catalyst into an extruder, melt-kneading the polylactic acid and the depolymerization catalyst together in said extruder, feeding said melt-kneaded product thereof from said extruder into a vent chamber maintained under a reduced pressure, depolymerizing the polylactic acid in said vent chamber, gasifying the formed lactide therein, and recovering the gasified lactide from said vent chamber, wherein the melt-kneaded product of the polylactic acid and the depolymerization catalyst melt-kneaded in the extruder are fed into said vent chamber through a discharge port of said extruder;

the temperature in said extruder is set so that the temperature of said melt-kneaded product is not higher than 270° C. at said discharge port; and an interior of said vent chamber is set so that the pressure is not higher than 8 kPaA and the temperature is 250 to 330° C. wherein an extrusion screw of the extruder does not extend into the vent chamber.

2. The method of recovering lactide according to claim 1, wherein the polylactic acid and the polymerization catalyst are thrown into said extruder but without throwing the carrier resin therein, and the melt-kneaded product of said polylactic acid is fed into said vent chamber without using the carrier resin.

3. The method of recovering lactide according to claim 1, wherein a trapping apparatus is linked to said vent chamber to trap the gasified lactide.

4. The method of recovering lactide according to claim 1, wherein said vent chamber is provided at the bottom portion thereof with a discharge pipe for discharging the residue from which the gasified lactide has been removed.

5. The method of recovering lactide according to claim 1, wherein said depolymerization catalyst is thrown into said extruder on the side downstream of the polylactic acid in the direction of extrusion in the extruder.

* * * * *